United States Patent [19]

Sorkin

[11] Patent Number: 4,808,174

[45] Date of Patent: Feb. 28, 1989

[54] CONDOM OF PLASTIC MATERIAL

[76] Inventor: Reuben Sorkin, 4721 University Dr., Coral Gables, Fla. 33146

[21] Appl. No.: 148,724

[22] Filed: Jan. 25, 1988

Related U.S. Application Data

[63] Continuation-in-part of Ser. No. 093,933, Sep. 8, 1987.

[51] Int. Cl.[4] ............................................. A61F 5/44
[52] U.S. Cl. .................................. 128/644; 604/352; 604/349
[58] Field of Search ................................ 604/347–353; 128/132 R, 138

[56] References Cited

U.S. PATENT DOCUMENTS

| | | | |
|---|---|---|---|
| 3,401,697 | 9/1968 | Lefley et al. | 604/352 |
| 3,677,225 | 7/1972 | Czirely | 604/352 |
| 4,432,357 | 2/1984 | Pomeranz | 604/349 |
| 4,735,621 | 4/1988 | Hessel | 604/349 |

FOREIGN PATENT DOCUMENTS 1158507 12/1983 Canada ................................ 604/349

Primary Examiner—Samuel Scott
Assistant Examiner—Noah Kamen
Attorney, Agent, or Firm—John Cyril Malloy

[57] ABSTRACT

A condom of plastic material which includes a tubular length having a closed first end and an open second end and an integral pubic shield about the open end with the tubular length being sized to jacket the penis of a user and the pubic shield being adapted to overlay the pubic area of a user. Preferably, the plastic material is selected from the class which includes polyethylene, polypropylene and vinyl.

8 Claims, 2 Drawing Sheets

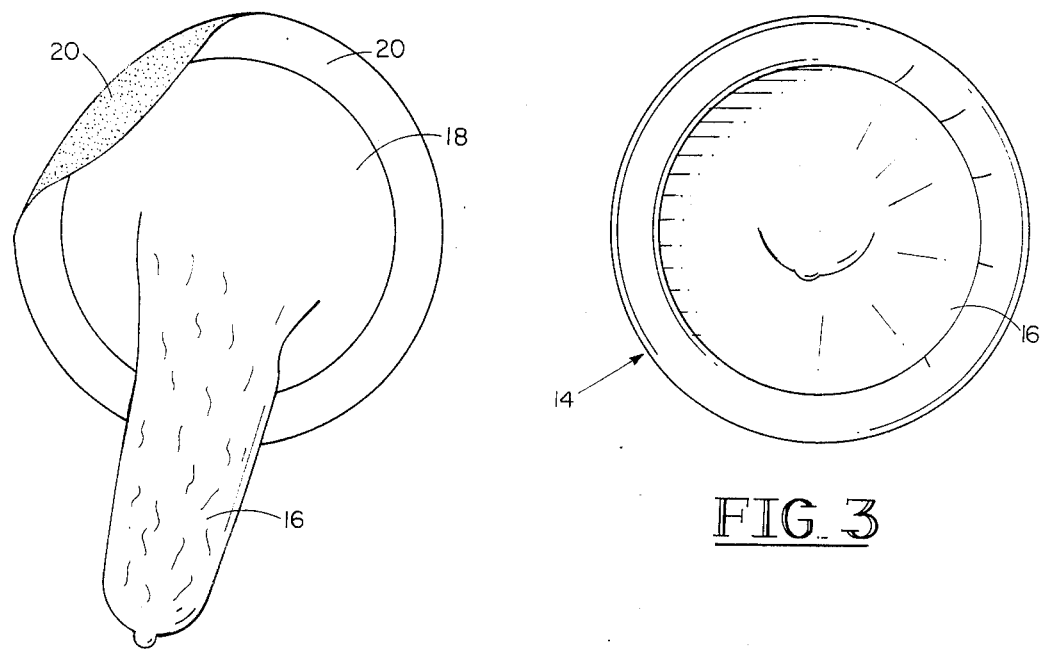
FIG. 2
FIG. 3
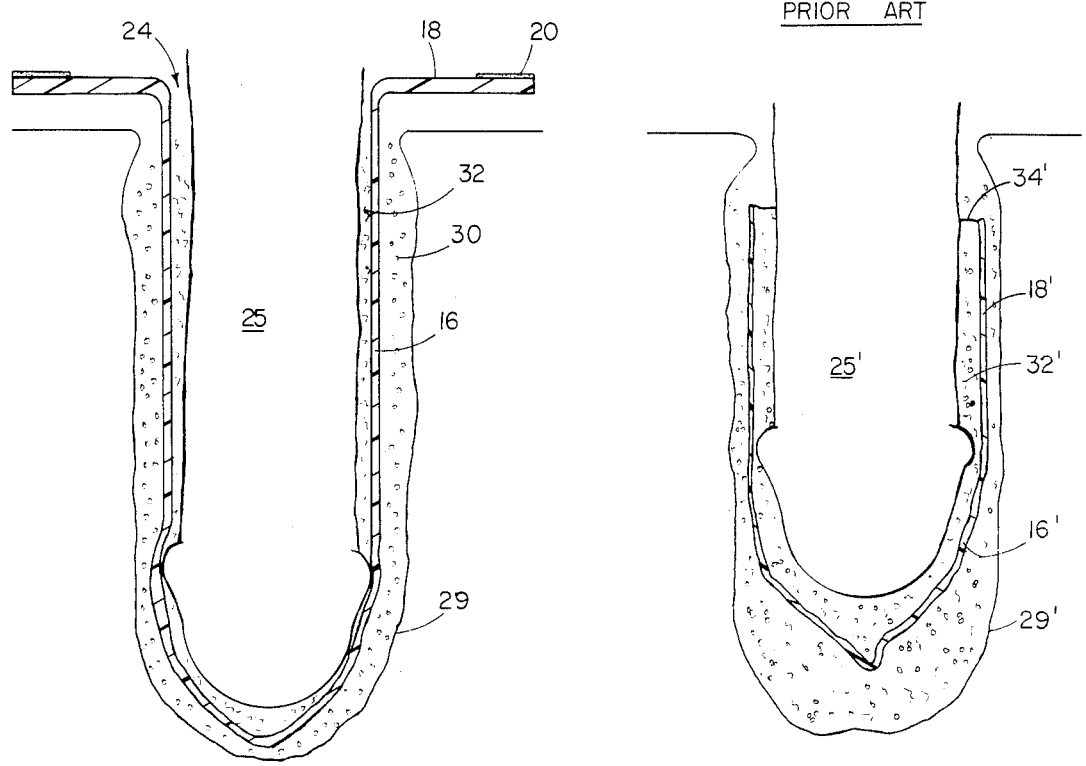
FIG. 4
PRIOR ART
FIG. 5

CONDOM OF PLASTIC MATERIAL

This application is a continuation-in-part of earlier filed U.S. patent application Ser. No. 07/093,933 filed Sept. 8, 1987.

FIELD OF THIS INVENTION

This invention relates to an integral condom of plastic material which includes a pubic shield, the plastic material being preferably selected from the class which includes polyethylene, polypropylene, and vinyl.

BACKGROUND OF THE INVENTION

There is a growing awareness of the seriousness of sexually transmitted diseases and the need for protection. Defects of latex condoms have become increasingly apparent. For example, it is established that about one-sixth of the users of latex condoms may nevertheless incur sexually transmitted diseases because of tears and improper use. This invention proposes a condom of plastic material preferably selected from the class of polypropylene, polyethylene and vinyl which greatly reduces the risk of sexually transmitted disease and provides extra prevention. This is highly desirable especially in view of the seriousness of diseases such as AIDS, Herpes, Syphilis, Gonorrhea, Chalasmydia and other sexually transmitted diseases.

There are deficiencies in latex condoms in that the same may slip off the male organ after ejaculation because the penis becomes flaccid and shrinks to its normal size. When this happens, both partners are exposed to sexually transmitted diseases as well as pregnancy. Because the vagina provides an ideal growth culture media of all kinds of venereal disease, vaginal fluids should be avoided. The ordinary condom does not provide a water-tight seal at the base to protect the pubic area of a user from exposure of his body to sexually transmitted diseases. Also, because latex condoms may tear during coitus. Further, latex condoms should be stored under ideal conditions, for example, they cannot be exposed to extreme heat or cold. Hence, the condom of plastic material of the present invention provides an alternative to latex and is an improved product. The plastic condom of the present invention is not adversely affected by products such as petroleum jelly which has a deliterious affect on latex condoms. Finally, latex and rubber condoms have a limited shelf life and, beyond this, become brittle and abrasive which is not typical of condoms of plastic material.

OBJECT OF THE PRESENT INVENTION

It is, therefore, an object of the invention to provide an improved thin-walled condom of plastic material, preferably selected from the class which includes polyethylene, polypropylene, and vinyl and comprises a tubular length having a closed first end and an open second end with the second end and tubular length being sized to jacket the penis of a user. Preferably, the condom also includes a pubic shield integral with it which is thicker than the material along the tubular length of the condom with the pubic shield provided protection for an enlarged zone about the base of the penis and wherein an adhesive is preferably applied to the pubic shield for attachment during coitus.

It is a general object of this invention to provide an improved condom of the type described more fully hereinafter which is inexpensive to manufacture, well adapted for avoiding sexually transmitted diseases and which is highly desirable in the present environment characterized by sexually transmitted diseases and which is strong and durable and does not sacrifice sexual sensuality.

In accordance with these and other objects which will become apparent hereinafter, the instant invention will now be described with reference to the accompanying drawings in which:

DESCRIPTION OF THE DRAWINGS

FIG. 2 illustrates the plastic condom prior to use.

FIG. 3 illustrates the plastic condom in a rolled condition.

FIG. 4 illustrates the plastic condom in use.

FIG. 5 is illustrative of problems which can occur with prior art condoms which do not have a pubic shield.

DETAILED DESCRIPTION OF THE PREFERRED EMBODIMENT

Figure 1:
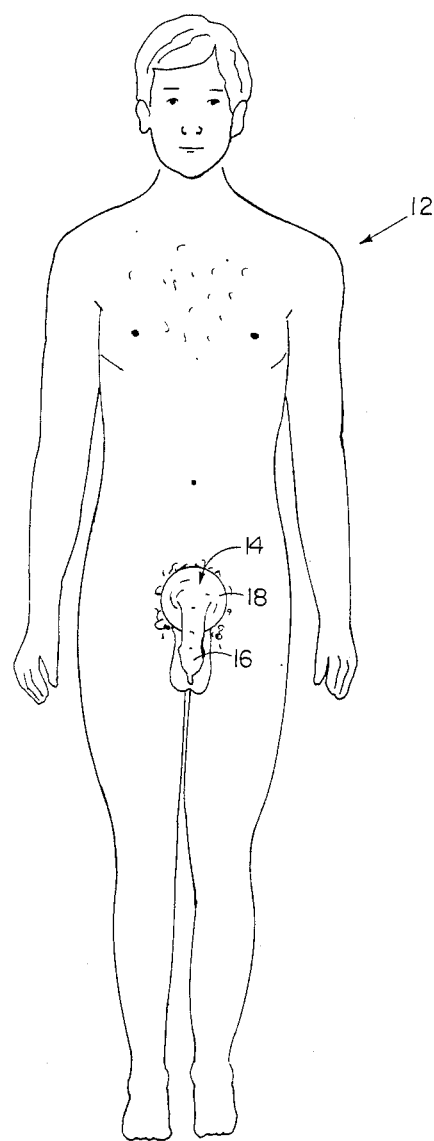
FIG. 1 illustrates an embodiment of the improved plastic condom on the body of a wearer.

The present invention relates to an improved condom of plastic which includes an integral pubic shield. FIGS. 1 and 2 illustrate one embodiment of the invention. In FIG. 3, the condom is shown rolled upon itself. It may, however, be provided in packages in a collapsed attitude. Preferably, the condom is provided in three sizes, small, medium and large.

In the several views, the numerals designate similar parts in the several figures.

In FIG. 1 a plastic condom 14 of the type to be described is shown on a wearer 12. The condom 14 includes a tubular portion 16, see FIG. 2. It has a rounded, closed distal end that may include a smaller diameter reservoir portion at the terminal end zone. The condom also includes a pubic shield 18 that is shown in a rolled stated in FIG. 3. In FIG. 3, the condom 14 is rolled onto itself and in FIG. 2 is shown in an unrolled attitude.

FIG. 1 shows the condom 14 disposed on the male user 12. In that figure, the pubic shield 18 is seen to protect the pubic area of the user. The tubular portion 16 has an open proximal end for inserting the penis 25 into a female opening 24. Preferably, a lubricant, such as the commercially available product, K.Y. jelly may be utilized on the exterior surface of the tubular portion 16 and, if desired, within the tubular portion. In a preferred embodiment, the condom is of one piece molded plastic construction and includes a shield for protecting the pubic area. Preferably, the condom is made of suitable plastic material such as polypropylene, polyethylene, or a thin vinyl. In use, the shield 18 is intended to overlay the pubic area of a user and particularly the scrotum in order to shield against vaginal and other fluids contacting the body of a user during intercourse.

Preferably, the shield 18 is of relatively thicker material than the thin walled portion 16 shown in FIG. 4. FIG. 4 shows that the shield extends radially outwardly from the tubular portion 16 at the proximal end at least a distance of one and one-half times the diameter of the opening at the proximal end. Preferably, the radial span of the shield is at least 2½ inches. The thickness of the shield may be between 0.07 mm. to 0.16 mm. A lubricant may be placed on the inside of the tubular portion 14 in order to assist the user in placing that portion onto his penis.

In addition to protecting the user from vaginal and other fluids 30 within the vagina 29 during intercourse, it is believed that after ejaculation and the collapse of the penis, the shield will better trap the ejaculated fluids and thereafter protect the other sexual partner from the male fluids 32.

Preferably, the interface between the tubular portion 16 and the shield 18 is reinforced since it is believed that significant stress will be present in that area. Preferably, the improved condom and shield is of one piece molded plastic selected from the class which includes polyethylene, polypropylene and vinyl.

Referring to FIG. 5, when the penis becomes flaccid, a conventional condom 16' which does not have a shield may creep into the vagina 29' in which event the male fluids 32' may mix as at 34' with the vaginal fluids as the penis 25' becomes flaccid and the tubular portion 18' tends to creep into the vagina 29'.

With the present invention during and after coitus, use of the condom of the present invention prevents exposure of the penis and vagina to infection, especially after ejaculation. In a preferred manufacture, onto a cylindrical mold, plastic material selected from the class which includes vinyl, polypropylene, and polyethylene is deposited and subjected to heat so that it flows forming a film on the mold core. The combination is then drawn through a cold bath where it sets up and is, thereafter, removed as a one piece molded plastic structure. Thereafter, the adhesive 20 is applied as a ring, preferably, about the outer periphery of the shield and a liner also indicated by the numeral 20, since it is transparent, overlays the adhesive. Preferably, the adhesive is of the type which is readily peeled from the body without pain. Such an adhesive or skin glue, as it is sometimes called in the field, is a copolymer of an acrylic ester and acrylic acid.

Plastic material such as that utilized in the manufacture of the foregoing condom structure is preferably translucent, is relatively thin and in the range of about 0.03 mm. This provides a strong condom tubular length which is impervious to water and air, which is also sufficient to prevent the passage of germs, bacteria or virus. Preferably, in the manufacture of the condom, fibrous material such as elongate strands of fine diameter fibers 17 as seen in FIG. 2 may be utilized for reinforcement and to strengthen the condom, especially the tubular portion.

In use with the condom, the penis is at all times out of contact with vaginal secretions which may contain infectious organisms. The plastic film has many times the tensile strength of latex and requires considerable force to break it. The shield portion protects the male organ by being attached to the pubic area using the painless adhesive which is commercially available from the Johnson & Johnson Company of New Brunswick, N.J. known as a First Aid Adhesive. The plastic is far less expensive than latex and an unlimited supply is available. Moreover, plastic material has a longer shelf life than conventional latex condoms and does not require ideal storage conditions. Plastic materials do not permit the passage of water or air and hence is impervious to infectious materials. Moreover, the plastic condom tubular length provides the same sexual sensuality as the latex condom and may be lubricated at the factory by commercially available K.Y. jelly inside or out, or both, before use. The jelly is preferably contained in a small aluminum packet provided with the condom. Since plastic is relatively inelastic, compared to latex, preferably it is provided in three sizes, small, medium and large. The plastic shield is a circular disk of about 5 inches in diameter and is part of the condom, that is, it is an integral construction. It can be manufactured by dipping a mold into a hot plastic solution, and, thereafter, cooling it and, later, applying a painless adhesive to the side that adheres to the pubic area of the wearer. Preferably, a liner is provided for the adhesive which can be peeled away.

As is well known, among the population there are male homosexuals and the greater strength and structure of a plastic condom provides more protection for those who engage in such activities. It is not essential for the shield to adhere to the male body in order to be effective; however, it is preferred that adhesive be used.

While the instant invention has been shown and described in what is considered to be a preferred embodiment, it is recognized that departures may be made therefrom within the spirit and scope of this invention which is therefore not to be limited except as set forth in the claims which follow and in accordance with the doctrine of equivalents.

What is claimed is:

1. A thin-walled one-piece condom of plastic material comprising fiber means that reinforce a polyethylene film including a tubular length having a closed first end and an open second end, said open second end and tubular length being sized to receive and jacket the penis of a user while erect.

2. The condom as set forth in claim 1 wherein said condom is of translucent material.

3. The condom as set forth in claim 1 wherein said condom includes an integral pubic shield extending radially from said open second end.

4. The condom as set forth in claim 3 wherein said pubic shield is relatively thick compared to the thickness of the tubular length.

5. The condom as set forth in claim 4 wherein said shield includes an inner surface facing in a direction common to that of said tubular length and an outer surface, and said outer surface includes an outer peripheral zone spaced from said tubular length, and said outer zone being spaced from said tubular length such that the distance across said shield and tubular portion is at least about 5 inches.

6. The condom as set forth in claim 5 wherein adhesive means are provided on said outer surface.

7. The condom as set forth in claim 6 wherein said adhesive is on said outer surface peripheral zone.

8. The condom as set forth in claim 7 wherein liner means are provided to removably overlay said adhesive.

* * * * *